(12) United States Patent
Komissarova

(10) Patent No.: US 8,128,961 B2
(45) Date of Patent: Mar. 6, 2012

(54) PHARMACEUTICAL COMPOSITION, THE USE THEREOF AND METHOD FOR PRODUCING SAID COMPOSITION

(76) Inventor: Irina Alekseevna Komissarova, Moscow (RU)

( * ) Notice: Subject to any disclaimer, the term of this patent is extended or adjusted under 35 U.S.C. 154(b) by 638 days.

(21) Appl. No.: 10/415,944

(22) PCT Filed: Nov. 28, 2001

(86) PCT No.: PCT/RU01/00513
§ 371 (c)(1),
(2), (4) Date: May 7, 2003

(87) PCT Pub. No.: WO02/43710
PCT Pub. Date: Jun. 6, 2002

(65) Prior Publication Data
US 2004/0029966 A1    Feb. 12, 2004

(30) Foreign Application Priority Data
Nov. 28, 2000  (RU) .................................. 2000129647
Aug. 20, 2001  (EA) .................................. 200100794

(51) Int. Cl.
*A61K 9/16*    (2006.01)
(52) U.S. Cl. ..................... 424/490; 424/493; 424/494
(58) Field of Classification Search ................ 424/400, 424/464, 465, 468, 489, 490
See application file for complete search history.

(56) References Cited

U.S. PATENT DOCUMENTS

| | | | |
|---|---|---|---|
| 3,873,713 A | 3/1975 | Haas | 424/280 |
| 4,016,254 A | 4/1977 | Seager | 424/33 |
| 4,327,076 A * | 4/1982 | Puglia et al. | 424/441 |
| 4,539,315 A | 9/1985 | Bender | 514/162 |
| 4,569,852 A * | 2/1986 | Yang | 426/534 |
| 4,981,698 A * | 1/1991 | Cherukuri et al. | 426/5 |
| 5,204,115 A * | 4/1993 | Olinger et al. | 424/470 |
| 5,534,262 A * | 7/1996 | Dobrotvorsky et al. | 424/464 |
| 5,575,987 A * | 11/1996 | Kamei et al. | 424/451 |
| 5,607,697 A * | 3/1997 | Alkire et al. | 424/495 |
| 5,683,722 A * | 11/1997 | Derrieu et al. | 424/493 |
| 5,976,577 A * | 11/1999 | Green et al. | 424/490 |
| 6,048,543 A * | 4/2000 | Schneider et al. | 424/442 |
| 6,328,994 B1 * | 12/2001 | Shimizu et al. | 424/489 |

FOREIGN PATENT DOCUMENTS

| | | | |
|---|---|---|---|
| JP | 411246393 A * | 9/1999 | |
| JP | 2000178183 A * | 6/2000 | |
| RU | 2025121 | 12/1994 | |
| SU | 1535369 | 1/1990 | |

OTHER PUBLICATIONS

"Pharmaceutical Formulation Technology," Edition by L.A. Ivanova. Moscow: Medicine, 1991, vol. 2, pp. 169-170, 182.

* cited by examiner

*Primary Examiner* — Susan Tran
(74) *Attorney, Agent, or Firm* — Gilman Pergament LLP

(57) ABSTRACT

This invention relates to the field of chemical pharmaceutical industry, namely, to pharmaceutical formulations for preparation of prolonged release tablets, in particular, tablets for sublingual application, and to methods of preparation of such formulations. Pharmaceutical formulation comprises 96.0 to 99.8% wt. of the pharmaceutical drug microcapsules, 0.1 to 1% wt. of lubricant, and 0.1 to 3% wt. of water, each microcapsule comprising 96.0 to 99.2% wt. of the pharmaceutical drug and 0.8 to 4% wt. of film-forming substance. Dispersant is also introduced into formulation in the amount of 0.1 to 10% wt. of the total mixture obtained. Method of preparation of the pharmaceutical formulation comprises preparation of microcapsules by deposition of coating of film-forming substance on non-agglomerated particles of pharmaceutical drug, and addition of lubricant and dispersant. In the course of preparation of the microcapsules and/or their intermediate storage moisture content in the coating is brought to concentration not more than 0.5% wt., and prior to addition of lubricant and dispersant microcapsules are moistened to water content of 0.1 to 3% wt. After introduction of lubricant, dispersant is added in the form of fine fraction of said pharmaceutical drug.

13 Claims, No Drawings

PHARMACEUTICAL COMPOSITION, THE USE THEREOF AND METHOD FOR PRODUCING SAID COMPOSITION

The present invention relates to the field of chemical pharmaceutical industry, namely, to pharmaceutical formulations for manufacturing of prolonged release tablets, in particular, tablets for sublingual administration, and to methods of preparation of such pharmaceutical formulations.

Microcapsules are formed by active principle deposited on insoluble core and coated with polymeric layer. This dosage form is intended for oral administration and has estimated disintegration time of 15 hours. Structure of the drug dosage form and its disintegration time prevent from its utilization in the drug dosage forms for sublingual application. Method of microcapsules manufacture provides for no features allowing regulation of disintegration time of the drug dosage form. Regulation of disintegration time is only possible by the way of changing microcapsule parameters and its coating.

There are known formulations for tablets manufacturing (U.S. Pat. No. 3,873,713, cl.424/184, 1975; U.S. Pat. No. 4,016,254, cl.424/497, 1977) comprising microcapsules made of the drug crystals coated with polymer material layer. Tablets are pressed from microcapsules compounded with auxiliary substances (excipients). Methods of preparation of the formulation comprise deposition of coatings of film-forming substances on the drug crystals, and addition of lubricants followed with tablets compressing. These solutions are not concerned with a problem of disintegration time regulation of the dosage form. Disintegration time is determined by structure of the dosage form obtained and addition of standard auxiliary substances.

The present invention is aimed at creation of pharmaceutical formulation for manufacturing of the prolonged release tablets having disintegration time up to 30 minutes and method for preparation of such formulation, which allows to regulate tablet disintegration time in the said range, in particular, on their sublingual administration, using pharmaceutical drug and water.

To solve this problem, pharmaceutical formulation is proposed comprising microcapsules, each being non-agglomerated particle of water soluble pharmaceutical drug having polymer coating of film-forming substance, dispersant (pharmaceutical drug crystals), and water.

In accordance with the present invention, said pharmaceutical formulation is made up at following components ratio, % wt.:

| | |
|---|---|
| microcapsules | 96.0-99.8 |
| lubricant | 0.1-1 |
| water | 0.1-3 | at dispersant content of 0.1 to 10% wt. of the mixture obtained, the pharmaceutical drug and film-forming substance content in microcapsule amounting to 96.0 to 99.2% wt. and 0.8 to 4% wt., correspondingly.

In accordance with the present invention, non-agglomerated particles of water soluble pharmaceutical drug used for film coating have dimensions of 200 to 700 micron.

Utilization of the larger particles allows to slow down dissolution process, and also to diminish concentration of auxiliary substances necessary for compressing the tablets. By changing the particles size, disintegration and tablet dissolution rate may be varied. In accordance with the invention, as a rule, the amount of particles having size of 200 micron and below shouldn't exceed 10% of the bulk substance.

When preparing the formulation, microcapsules are made beforehand by applying a coating layer of natural or synthetic polymers on non-agglomerated particles of water soluble pharmaceutical drug. In the process of microcapsules preparation water content in the coating is brought to concentration below 0.5% wt. Reduction in moisture content of microcapsules is also possible during their intermediate storage.

To prepare pharmaceutical formulation of this invention, microcapsules having moisture content below 0.5% wt. are moistened to the water content of 0.1 to 3% wt. The moistening is carried out to swelling of polymeric coating of the microcapsules. After that, lubricant is introduced, and then dispersant as fine fraction of the pharmaceutical drug.

Drying and subsequent moistening of microcapsules in the course of tablet mixture preparation impart more regular form to the microcapsules coating and exert positive effect on structure homogeneity of the dosage forms manufactured, providing for possibility of stabilization of the tablets disintegration indices.

Water content in the range of 0.1 to 3% wt. provides for the swelling of polymeric coating and results in the structure of the polymeric coating, which was of flaky texture after deposition in fluidized bed apparatus, becoming a continuous one. Such structure of polymeric coating is preserved in the tablet obtained, ensuring increase in the tablet disintegration time due to decrease in the coating permeability.

Introduction of dispersant into the formulation imparts porosity to the tablets and facilitates a decrease in their disintegration time. At the same time, change of the dispersant concentration and utilization of fine fraction of the pharmaceutical drug as dispersant allow to regulate disintegration time of the dosage form and to maintain high content of the pharmaceutical compound in the preparation without addition of traditional adjuvants.

In accordance with this invention, pharmaceutical drug serves as dispersant. In such a way, both the substance being the active principle of the tablet and the dispersant have identical physical parameters. Owing to this reason (in particular, to equal solubilities of dispersant and pharmaceutical drug in the formulation of microcapsule) gradual dissolution of the tablet is achieved with release of the pharmaceutical substance rather than fast disintegration into its constituent particles, without increase in total dissolution surface.

To obtain coating, cellulose ethers may be used, which are soluble in water or mixture of water with organic solvent.

Coating layer is deposited on the non-agglomerated particles of pharmaceutical drug in fluidized bed apparatus.

As lubricant, stearic acid or its pharmaceutically acceptable salts, as well as mixtures of stearic acid and its salts.

As pharmaceutical drug, aminoacetic acid or xylitol may be used, or other crystalline water-soluble substances.

To obtain pharmaceutical formulation of this invention for manufacturing of the dosage form of preparation, in particular, comprising as pharmaceutical drug aminoacetic acid (crystalline water-soluble substance), at first microcapsules are prepared, each being a non-agglomerated particle of aminoacetic acid coated with a shell of the film-forming substance, in which capacity, for example, methylcellulose is used, as follows:

preparation of crude material for microcapsules is accomplished using 1.24 kg of methylcellulose per 100 kg of aminoacetic acid;

1.2% aqueous solution of methylcellulose is prepared in the reactor equipped with heating jacket and mixer or in reservoir with hand stirring, the solution obtained is left to stand until full swelling of methylcellulose, and then cooled and filtered to remove clots;

preparation of pharmaceutical drug is carried out by sifting of crude material to separate particles of specified size;

aminoacetic acid is brought into fluidized state, and then methylcellulose solution is fed into fluidized bed apparatus at 35-42° C. with air-spraying nozzle to secure deposition of methylcellulose coating on non-agglomerated particles of aminoacetic acid;

after completing the feeding of methylcellulose solution, the bulk is dried to residual moisture of 0.5% wt.; and product is discharged and separated from agglomerates and lumps. At that, specified fraction may be isolated.

The finished product obtained as described above is loaded into containers for temporary storage before further processing. Methylcellulose content in the finished product equals to 1±0.1%, and moisture—up to 0.5% of the total weight.

After that, mixture for tablets pressing (tableting mixture) is compounded on basis of the microcapsules prepared. The compounding of this mixture is accomplished by 10 kg batches. To this purpose, strained microcapsules of 200 to 700 micron size are moistened in mixer with water and then placed in closed container for a time period sufficient for swelling of the polymeric coating and formation of semi-product with residual moisture of 0.2 to 0.8% wt.

After moistening, the bulk material is prepared for tableting. To this purpose, a part of the moistened material (about 1 kg) is picked up and mixed in separate container with lubricant, in which capacity magnesium stearate may be used, introduced in small portions with thorough mixing. At that, total weight of the lubricant amounts usually to 0.097 kg. After that, mixture comprising microcapsules and lubricant is blended with remainder (about 9 kg) of moistened microcapsules.

To regulate tablet disintegration time, dispersant is introduced to tableting mixture in the amount of 0.1-10%, that is, 10 to 100 g of dispersant may be used per 1 kg of bulk material. As dispersant, fine fraction of pharmaceutical drug is used, which is an active principle.

After that, bulk material prepared in such a way is sifted. Sifting may be performed also after introduction of lubricant, prior to dispersant. Both components may be also introduced after sifting.

The tableting mixture prepared is pressed with automated tablet-compressing machine equipped with punch of 6 mm diameter providing for manufacturing of tablet having weight of 0.102±7.5%

In the process of compression mean tablet weight, tablets dimensions, their appearance, and disintegration times are checked at least once every hour. On deviation of the press from these parameters, loading and weight adjustment is performed.

Tablet manufactured as described above, comprise aminoacetic acid—0.1 g, water-soluble methylcellulose—0.001 g, and magnesium stearate (magnesium salt of stearic acid)—0.001 g.

Mean weight of the tablet obtained is 0.102 g±7.5%, with tablet being of plano-cylindrical form with 2.6±0.3 mm height and 6±0.2 mm diameter. Tablets prepared by the method of this invention satisfy established specifications as to appearance. Typical of the tablet obtained is white coloring with mottled elements.

Disintegration time of the aminoacetic acid tablets obtained amounts to up to 30 min.

The process flow described is common for different water-soluble crystalline pharmaceutical substances, and in certain cases individual parameters may vary, such as fluidization temperature, concentration of the moistening liquid, and treatment time for crystals coating. Utilization of pharmaceutical drug particles of 200 to 700 micron size ensures sublingual application of the tablets manufactured as described above.

Feasibility of realization of this invention is confirmed with following examples.

EXAMPLE 1

100 kg of aminoacetic acid are placed into fluidized bed apparatus for deposition of coating. The substance is moistened with 1.2% solution of methylcellulose (M-100 grade) for 4-5 hours at 42° C. After completion of the process, product is dried to residual moisture of 0.1% wt., dusted with magnesium stearate and mixed with dispersant, comprising fine fraction of the active principle, in the quantity of 5% wt.

Composition of the obtained semi-product—mixture for tablets pressing (tableting mixture) is presented in Table 1. Corresponding physicochemical parameters for the tablets (6 mm, 0.102 g) are listed in Table 2.

TABLE 1

| Ingredient | Composition, % wt. |
|---|---|
| Aminoacetic acid | 97.9 |
| Methylcellulose | 1 |
| Magnesium stearate | 1 |
| Water | 0.1 |

TABLE 2

| Tablets physicochemical parameters | Results of analysis |
|---|---|
| Disintegration time, min. | 8 |
| Strength, H | 25 |
| Abrasion strength, % | 0.3 |
| Appearance | of white color, with mottled elements |

EXAMPLE 2

Microcapsules prepared analogous to Example 1, are moistened to water content of 0.7% wt., dusted with magnesium stearate, after which fine fraction of the active principle is introduced in the amount of 5% wt. Composition of the formulation obtained is listed in Table 3. Physicochemical parameters of the corresponding tablets (6 mm, 0.102 g) are presented in Table 4.

TABLE 3

| Ingredient | Composition, % wt. |
|---|---|
| Aminoacetic acid | 97.3 |
| Methylcellulose | 1 |
| Magnesium stearate | 1 |
| Water | 0.7 |

TABLE 4

| Tablets physicochemical parameters | Results of analysis |
|---|---|
| Disintegration time, min. | 22 |
| Strength, H | 30 |
| Abrasion strength, % | 0.1 |
| Appearance | of white color, with mottled elements |

EXAMPLE 3

100 kg of xylitol are placed into fluidized bed apparatus. To deposit film coating, the substance is moistened with 3.0% solution of methylcellulose (M-100 grade) in a manner analogous to Example 1. After completion of the process, product is dried to moisture content not more than 0.1% wt. and dusted with magnesium stearate. Then dispersant is introduces analogous to Example 1. Composition of the formulation obtained is presented in Table 5, and physicochemical parameters of corresponding tablets—in Table 6.

TABLE 5

| Ingredient | Composition, % wt. |
|---|---|
| Xylitol | 96.7 |
| Methylcellulose | 3 |
| Magnesium stearate | 0.2 |
| Water | 0.1 |

TABLE 6

| Tablets physicochemical parameters | Results of analysis |
|---|---|
| Disintegration time, min. | 10 |
| Strength, H | 22 |
| Abrasion strength, % | 0.3 |
| Appearance | of white color, with mottled elements |

EXAMPLE 4

Semi-product obtained analogous to Example 3 is moistened to moisture content of 0.3% wt. and dusted with magnesium stearate. Composition of the formulation obtained is presented in Table 7, and corresponding physicochemical properties—in Table 8.

TABLE 7

| Ingredient | Composition, % wt. |
|---|---|
| Aminoacetic acid | 96.5 |
| Methylcellulose | 3 |
| Magnesium stearate | 0.2 |
| Water | 0.3 |

TABLE 8

| Tablets physicochemical parameters | Results of analysis |
|---|---|
| Disintegration time, min. | 12 |
| Strength, H | 32 |
| Abrasion strength, % | 0.15 |
| Appearance | of white color, with mottled elements |

EXAMPLE 5

100 kg of aminoacetic acid is placed into fluidized bed apparatus for deposition of film coating. The substance is moistened with 3% solution of methylcellulose (M16 grade) in a manner analogous to described in Example 1.

After completion of the process, product is dried to moisture content of 3% wt., dusted with 1% wt. of magnesium stearate, and mixed with dispersant 10% wt. Composition of the formulation obtained (tableting mixture) is presented in Table 9, and physicochemical properties of the tablets (6 mm, 0.102 g)—in Table 10.

TABLE 9

| Ingredient | Composition, % wt. |
|---|---|
| Aminoacetic acid | 92 |
| Methylcellulose | 4 |
| Magnesium stearate | 1 |
| Water | 3 |

TABLE 10

| Tablets physicochemical parameters | Results of analysis |
|---|---|
| Disintegration time, min. | 30 |
| Strength, H | 48 |
| Abrasion strength, % | 0.1 |
| Appearance | of white color, with mottled elements |

EXAMPLE 6

100 kg of aminoacetic acid are placed into fluidized bed apparatus for deposition of the film coating. The substance is moistened with 0.8% solution of methylcellulose (grade 100) for a period of 4-5 hours at bed temperature of 42° C. After completion of the process, product is dried to a moisture content of 0.1% wt., dusted with magnesium stearate in the amount of 0.1% wt., after which fine fraction of aminoacetic acid is added as dispersant in the amount of 0.1% wt.

Composition of the formulation obtained (tableting mixture) is presented in Table 11, and physicochemical properties of the tablets (6 mm, 0.102 g)—in Table 12.

TABLE 11

| Ingredient | Composition, % wt. |
|---|---|
| Aminoacetic acid | 99 |
| Methylcellulose | 0.8 |

TABLE 11-continued

| Ingredient | Composition, % wt. |
| --- | --- |
| Magnesium stearate | 0.1 |
| Water | 0.1 |

TABLE 12

| Tablets physicochemical parameters | Results of analysis |
| --- | --- |
| Disintegration time, min. | 6 |
| Strength, H | 20 |
| Abrasion strength, % | 0.35 |
| Appearance | of white color, with mottled elements |

The invention claimed is:

1. A pharmaceutical composition for prolonged release of an active principle substance, said pharmaceutical composition comprising:
   a) microcapsules comprising non-agglomerated particles of said active principle substance having a coating of a film-forming substance, wherein said microcapsules comprise 96.0-99.2 wt. % of said active substance and 0.8-4 wt. % of said film-forming substance, said microcapsules being present in the amount of 99 wt. % of said composition;
   b) a lubricating substance in the amount of 0.1-1 wt. % of said composition;
   c) water in the amount of 0.1-3 wt. % of said composition; and
   d) 0.1 to 10 wt. % of a dispersant in the form of the active principle substance;
   wherein the active principle substance comprises aminoacetic acid.

2. The composition according to claim 1, wherein said film-forming substance is cellulose ethers soluble in water or organic solvent, or a mixture thereof.

3. The composition according to claim 1, wherein said lubricating substance is stearic acid, its pharmaceutically acceptable salt, or mixture thereof.

4. The composition according to claim 1, wherein the size of said non-agglomerated particles is 200-700 micron.

5. A process for manufacturing a tablet of the composition of claim 1, said process comprising the steps of:
   forming said microcapsules by covering said non-agglomerated particles of said active principle substance with said film-forming substance,
   drying said microcapsules to residual moisture below 0.5% wt.,
   moistening said microcapsules with 0.1 to 3 wt. % of water to cause swelling of said coating,
   introducing said lubricating substance,
   introducing said dispersant in the form of particles of said active principle substance to form a tabletting mixture, and
   compressing the tabletting mixture into said tablet.

6. The composition of claim 1, which has disintegration time of up to 30 minutes.

7. The composition of claim 2, which has disintegration time of up to 30 minutes.

8. The composition of claim 3, which has disintegration time of up to 30 minutes.

9. The composition of claim 4, which has disintegration time of up to 30 minutes.

10. The composition of claim 1, which is formulated for sublingual administration.

11. The composition of claim 1, wherein said film-forming substance is methyl cellulose.

12. The composition of claim 1, wherein 10% or less of said non-agglomerated particle have particle size less than 200 microns.

13. The composition of claim 1, wherein the ratio of said dispersant to the combined weight of said components a), b), and c) is ranging from 1:100 to 1:10.

* * * * *